US009265848B2

(12) United States Patent
Lejeune et al.

(10) Patent No.: US 9,265,848 B2
(45) Date of Patent: Feb. 23, 2016

(54) SYSTEM FOR PROTECTING A CONTAINER TREATMENT DEVICE BY MEANS OF AN ELECTRON BEAM

(75) Inventors: Philippe Lejeune, Quimper (FR); Philippe Macquet, Quimper (FR)

(73) Assignee: HEMA, Quimper (FR)

( * ) Notice: Subject to any disclaimer, the term of this patent is extended or adjusted under 35 U.S.C. 154(b) by 0 days.

(21) Appl. No.: 13/513,655

(22) PCT Filed: Dec. 3, 2010

(86) PCT No.: PCT/EP2010/068882

§ 371 (c)(1), (2), (4) Date: Sep. 13, 2012

(87) PCT Pub. No.: WO2011/067393
PCT Pub. Date: Jun. 9, 2011

(65) Prior Publication Data

US 2013/0001434 A1 Jan. 3, 2013

(30) Foreign Application Priority Data

Dec. 3, 2009 (FR) ..................................... 09 58648

(51) Int. Cl.

*A61L 2/00* (2006.01)
*A61L 2/08* (2006.01)
*B65B 55/08* (2006.01)

(52) U.S. Cl.

CPC ................ *A61L 2/087* (2013.01); *B65B 55/08* (2013.01); *A61L 2202/15* (2013.01); *A61L 2202/23* (2013.01)

(58) Field of Classification Search

USPC .......................... 250/453.11, 454.11, 455.11

See application file for complete search history.

(56) References Cited

U.S. PATENT DOCUMENTS

| | | | | |
|---|---|---|---|---|
| 6,668,877 | B2 | 12/2003 | Fehland et al. | |
| 6,690,020 | B2 | 2/2004 | Loda | |
| 7,767,987 | B2 * | 8/2010 | Eguchi et al. | 250/492.3 |
| 2008/0073549 | A1 | 3/2008 | Avnery | |
| 2009/0045350 | A1 | 2/2009 | Humele et al. | |

FOREIGN PATENT DOCUMENTS

| | | | |
|---|---|---|---|
| WO | 98/42385 | A1 | 10/1998 |
| WO | 2005002973 | A1 | 1/2005 |

* cited by examiner

*Primary Examiner* — Nicole Ippolito
*Assistant Examiner* — Hanway Chang
(74) *Attorney, Agent, or Firm* — Bachman & LaPointe, P.C.

(57) ABSTRACT

A treatment device for sterilizing containers by an electron beam includes a carousel that comprises a rotary holding plate supporting a plurality of treatment stations, each station including a sterilization device comprising an electron beam emitter, and a holding device for holding a container under the emitter. The treatment device includes a protection system for stopping the rays emitted by the emitters, the protection system comprises an annular segment-shaped, open stationary channel that is mounted in a stationary manner under the holding plate and forms, with the latter, a protective chamber in which the holding device supporting the containers moves, the channel having an open upstream end, for the inlet of the containers to be treated into the protective chamber, and an open downstream end, for the outlet of the treated containers from the chamber.

12 Claims, 2 Drawing Sheets

SYSTEM FOR PROTECTING A CONTAINER TREATMENT DEVICE BY MEANS OF AN ELECTRON BEAM

BACKGROUND

This invention relates to a treatment device for sterilising containers by means of an electron beam, said device being provided with a particular protection system.

It is known, in particular by document U.S. Patent 2009/0045350, treatment devices comprising a rotary carousel comprising a rotary holding plate supporting a plurality of treatment stations arranged with regular angular spacing, each treatment station comprising sterilisation means which comprise an electron beam emitter, and holding means to hold a container under said emitter, said emitter being able to emit an electron beam passing through the upper opening of a container supported by said holding means, in order to sterilise the container, in particular the inner wall of said container.

In relation to a conventional chemical sterilisation, sterilisation by means of an electron beam is more effective in terms of sterilisation, is faster, and does not leave any residual traces after treatment.

Electron beam emitters however produce undesirable rays, in particular X rays, and therefore require shielding or protection systems to be provided in order to prevent any risk of propagation of rays towards the exterior, and as such protect the operators. The protection systems are formed by a protective chamber made from a lead base, wherein is placed the rotary carousel for the sterilisation, as well as the container infeed and discharge starwheels. Such protection systems are heavy, cumbersome, and very expensive.

SUMMARY OF THE INVENTION

The purpose of this invention is to propose a treatment device for sterilising containers before filling, aiming to overcome the aforementioned disadvantages, that performs well and is fast, while still remaining simple in design and implementation.

To this effect, this invention proposes a treatment device for sterilising containers by means of an electron beam, comprising a carousel comprising a rotary holding plate, mounted in a rotating manner on a stationary frame, supporting a plurality of treatment stations arranged with regular angular spacing, each treatment station comprising sterilisation means, which comprise an electron beam emitter, and holding means to hold a container under said emitter, said emitter being able to emit an electron beam passing through the upper opening of a container supported by said holding means in order to sterilise said container, in particular the inner wall of said container, and a protection system for stopping the rays emitted by the emitters, characterised in that said protection system comprises an open stationary channel, in the form of a ring-shaped segment, more preferably of transversal section with a general U or V shape, mounted in a stationary manner under said holding plate and forming with the latter an ring-shaped segment protective chamber wherein the holding means supporting the containers moves, said channel having an open upstream end for the inlet of the containers to be treated into the protective chamber and an open downstream end for the outlet of the treated containers from the chamber.

According to the invention, the sterilisation is carried out by means of an electron beam and the protection system comprises a stationary channel forming with a rotary holding plate a ring-shaped segment protective chamber wherein the emitters will be activated in order to carry out the sterilisation operations. In comparison with chambers encompassing the entire device, the protective chamber according to the invention is simple in design and simple to produce, less expensive and less cumbersome.

According to an embodiment, said stationary channel is substantially without contact with said holding plate, said protection system comprising a first system of baffles to shield against the rays emitted by the emitters at the plate-ring liaison, said first system of baffles comprising for example two vertical ribs extending vertically from the lower face of the plate, between which the channel is positioned.

According to an embodiment, said protection system comprises a second system of baffles to shield against the rays that can pass through the upstream and downstream ends of the channel.

According to an embodiment, the device further comprises a first transfer starwheel, to transfer the containers to be treated to the holding means upstream of the upstream end, and a second transfer starwheel to remove the treated containers from the holding means downstream of the downstream end. Said second system of baffles can include a substantially vertical lateral wall extending from the outer wall of the channel, on either side of the upstream and downstream ends, and surrounding the two transfer starwheels.

Advantageously, the elements that comprise the protection system are made with a lead base.

According to a particularity, said emitter is provided with a tubular base nozzle, also called an antenna, able to extend substantially vertically under the holding plate and to deliver via its distal end the electron beam created by the emitter, each treatment station comprising means of raising/lowering, mounted above the plate, acting on said holding means and/or on said emitter in order to introduce said nozzle in the container, via its upper opening, or to extract said nozzle from the container. According to an embodiment, the emitter is mounted in a stationary manner on the plate, its nozzle extending vertically under the plate, the means of raising/lowering being able to move said holding means.

BRIEF DESCRIPTION OF THE DRAWINGS

The invention shall be better understood, and other purposes, details, characteristics and advantages shall appear more clearly when reading the following detailed explanatory description of a particular currently preferred embodiment of the invention, in reference to the annexed diagrammatical drawings, wherein.

DETAILED DESCRIPTION OF THE PREFERRED EMBODIMENT(S)

Figure 1:
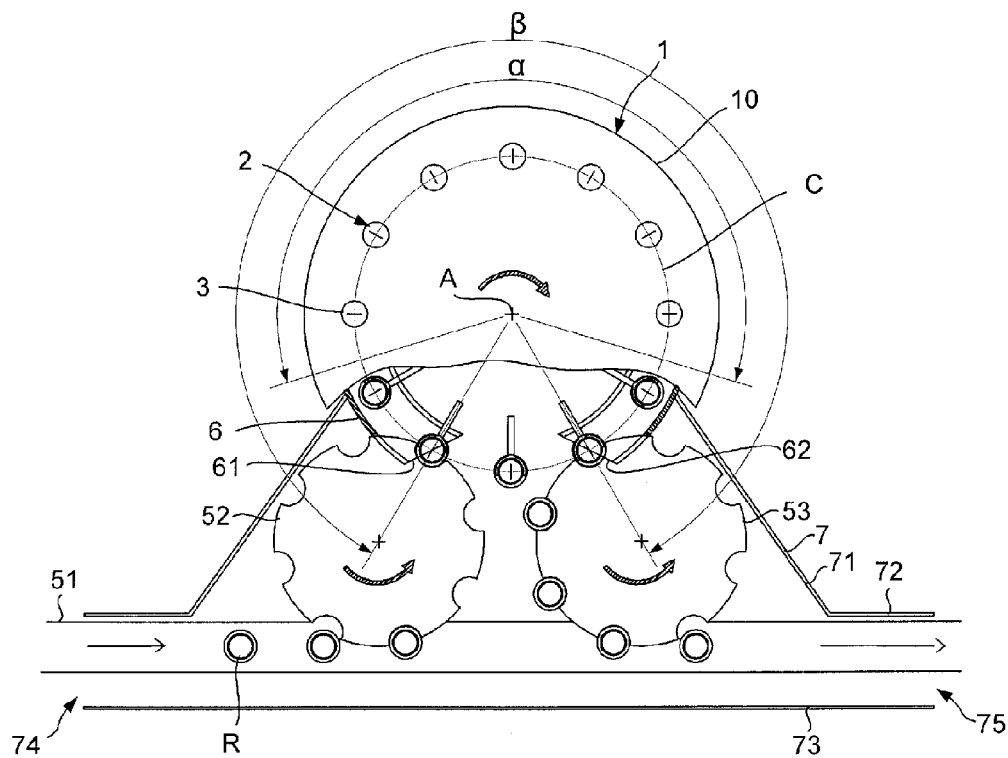
FIG. 1 is a schematic top view of a treatment device according to the invention, with a cut-out view of the holding plate of the carousel.
Figure 2:
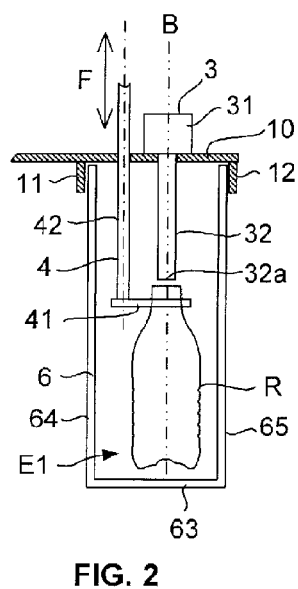
FIG. 2 is a partial diagrammatical radial cross-section view of the carousel on a treatment station, the nozzle of the emitter being arranged outside of the container.
Figure 3:
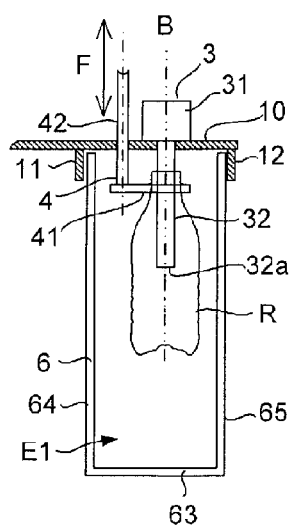
FIG. 3 is a view analogous to FIG. 2, with the nozzle of the emitter being inserted into the container.

FIGS. 1 to 3 show a treatment device for sterilising containers R, making it possible to sterilise the inner wall of the containers, by passing through the upper opening of the containers, for example bottles. The device for sterilising is intended to be placed upstream of a device for the filling of containers with a filling product, for example a liquid product such as water, milk or fruit juice. Of course, the invention can be applied to the sterilisation before filling of any type of container comprising a main upper opening, with any type of product, liquid or viscous.

The device comprises a carousel 1 comprising a holding plate 10, in the shape of a circular or annular plate, intended to be mounted in a turning manner on a stationary frame (not shown) around an axis A of vertical rotation, for example in a clockwise direction, such as is shown in FIG. 1. The holding plate supports a plurality of treatment stations 2 arranged with regular angular spacing around the axis A of rotation.

Each treatment station comprises sterilisation means 3 formed of an electron beam emitter 31, known per se, provided with a tubular nozzle 32 or tubular antenna, of extended shape, the emitter being able to deliver an electron beam via the distal end 32a of its nozzle. The distal end of the nozzle is provided with a sheet of titanium, for example with a thickness of 12 μm. The sterilisation means are for example formed of an emitter such as described in patent document US 2008/0073549. The emitter is mounted in a stationary manner on the upper face of the plate. Its nozzle, of longitudinal vertical axis B, passes through an opening of the plate 10 and extends under the lower face of the plate. The nozzle is defined in such a way that it can be inserted via the upper opening of the containers in order to irradiate the interior of the containers. The nozzles are arranged in such a way that their axes B are arranged according to a circle C.

Each filling station further comprises holding means 4 of a container R for the maintaining of a container under the emitter, centred according to the axis B of the nozzle. The holding means include for example a clamp 41 able to grasp the container, for example above or below its flange located at the base of its neck. The clamp is mounted on a vertical rod 42 via which the holding means are mounted on the plate 10. The rod is mounted in a sliding manner in an opening of the plate and comprises an upper portion extending above the plate.

This upper portion of the rod is connected to means of raising/lowering (not shown) making it possible to displace the clamp in vertical translation, such as is shown by the arrow F, between a low position shown in FIG. 2, wherein the distal end 32a of the nozzle 32 is arranged above the container, and a high position wherein the nozzle is inserted into the container for the sterilisation operation of the inner wall of the container.

The device comprises a container feed system, known per se, such as a belt conveyor 51 combined with a rotating transfer conveyor, conventionally referred to as a transfer starwheel 52, which makes it possible to laterally engage the containers between the clamps of the holding means of the treatment stations, and a system for removal, comprising a transfer starwheel 53 combined for example with a downstream portion of the aforementioned belt conveyor 51, making it possible to laterally remove the sterilised containers.

The device according to the invention comprises a shielding or protection system for stopping the rays emitted by the emitters, in particular parasitical rays of the X ray type.

This shielding system comprises a channel 6 mounted in a stationary manner under the plate 10, for example fixed to the frame of the carousel 1. This channel is open and therefore has the shape of an annular or ring-shaped segment extending over an angular sector of angle β, with an open upstream end 61 and an open downstream end 62. The channel has a transversal section with a general substantially U or V shape. In the embodiment, the channel is substantially in the shape of a U and is formed of a bottom wall 63, an inner cylindrical wall 64 and an outer cylindrical wall 65. The channel is stationary in such a way that the free edges of its cylindrical walls are arranged in the vicinity of the lower face of the plate, without contact with the latter, its bottom wall being arranged substantially parallel to said plate. The channel is substantially centred according to the circle C described by the axes B of the nozzles.

The plate 10 and the channel 6 are made from a lead base, and together form a protective chamber E1, in the shape of an annular segment extending over the angular sector of angle β, for example approximately 300° in the embodiment shown.

The plate is provided with two annular ribs 11, 12 between which are positioned the cylindrical walls 64, 65 of the channel, substantially without contact, so as to form a system of baffles preventing any propagation of rays on the channel-plate interface.

The transfer starwheel 52 transfers the containers to the clamps, immediately upstream of the upstream end 61, the clamp being in low position. The phase of sterilisation is carried out on an angular sector of angle α which is less than the angular sector of angle β. For each treatment station, the emitter can be activated when the clamp is in low position, in order to irradiate the outer wall of the container. The clamp is then displaced progressively towards its low position, then raised towards its high position in order to irradiate the entire inner wall of the container, said container being confined in the protective chamber E1. The length of the nozzle 32 and the height of the chamber E1 can be adapted, in such a way that the distal end 32a of the nozzle is arranged in the vicinity of the bottom of the container R in the high position of the clamp 41. The treated containers are then recovered by the transfer starwheel, immediately downstream of the downstream end 62 of the channel.

In order to increase the angle α whereon the treatment is carried out, while still preventing the risks of propagation of rays, the protection system comprises a system of baffles, also made of lead, to shield against the rays that can exit through the open ends 61, 62 of the stationary channel. This system of baffles, comprises a substantially vertical lateral wall 7 extending from the outer wall 65 of the channel, on either side of the ends of the channel, by surrounding the two transfer starwheels 52, 53, with passages 74, 75 for the inlet and the outlet of the containers. Said lateral wall comprises two first portions extending from the outer wall of the channel and each extending by a second portion 72 parallel to the conveyor 51, a third portion 73 is arranged on the external side of said conveyor, parallel to the second portions 72, the second portions forming with the third portion said passages 74, 75 for the inlet and outlet of the containers in the device. According to an embodiment, this system of baffles comprises a horizontal upper wall and a horizontal lower wall (not shown), arranged respectively above and below the transfer starwheels, and connected to the lateral wall.

Figure 4:
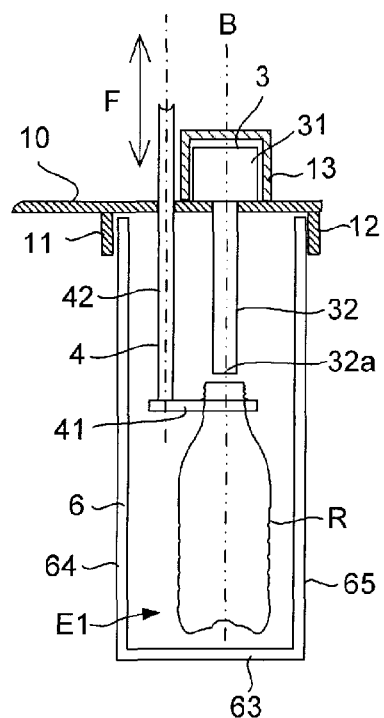
FIG. 4 is a diagrammatical view analogous to that in FIG. 2, showing a first alternative embodiment; and, FIG. 5 is a diagrammatical view analogous to that in FIG. 2, showing a second alternative embodiment.

FIG. 4 shows a treatment device according to an alternative embodiment, which is differentiated from the treatment device shown in FIGS. 1 to 3 by the fact that the emitters 31 mounted on the upper face of the plate 10 are covered with a cover 13 in order to stop any rays emitted directly by the emitters, in addition to the rays emitted by the nozzles of the emitters. Each emitter is covered with a tubular-shaped cover 13, made from a lead base, with a tubular peripheral wall, for example of circular transversal section, closed at its upper end by an upper wall. The tubular cover is placed on the emitter, with its lower edge coming against the upper face of the plate, and is assembled to the plate for example in a removable manner. The cover has a passage (not shown) for the electrical connection of the emitter. Alternatively, a single annular cover covers all of the emitters. The annular cover has for example a transversal section substantially in the general shape of a U, and is formed of an upper wall, an inner cylindrical wall and outer cylindrical wall.

Figure 5:
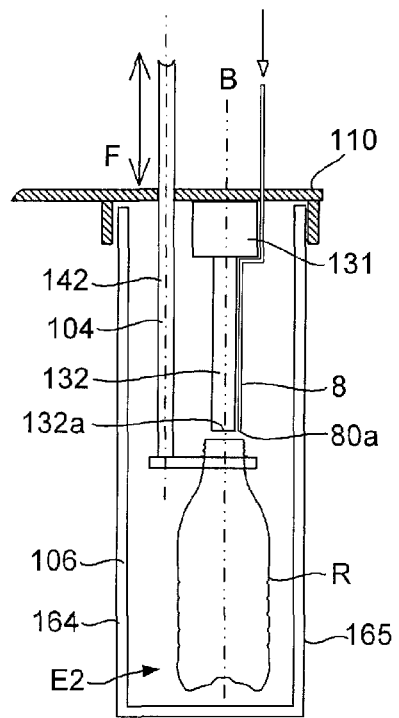

The FIG. 5 shows a treatment device according to a second alternative embodiment, wherein the emitters 131 are mounted on the lower face of the plate 110 of the carousel, in such a way that the emitters are placed in the protective chamber E2, formed as previously by a channel 106 mounted in a stationary manner under the plate 110. In order to make possible this positioning of the emitters in the chamber, the treatment device differs from that shown in FIGS. 1 to 3 by the fact that the inner cylindrical wall 164 and the outer cylindrical wall 165 of the channel are of greater height, and that the vertical rod 142 of the holding means 104 is of greater length.

Sterilisation by means of an electron beam can generate a small quantity of ozone in the chamber, in particular in the container placed in the chamber. According to an embodiment, the treatment device comprises injection means that are able to inject a product into the chamber, and in particular in the container, during and/or after the irradiation by means of an electron beam, in order to remove the ozone generated during the irradiation by the electron beam emitters, and as such prevent any deterioration by the ozone of the filling product which will be packaged in the containers. The injected product is a gaseous product or a liquid product with a low boiling point, in particular a neutral gas such as nitrogen, or liquid nitrogen. Advantageously, said injection means include a tubing or injection cock for each treatment station, extending more preferably along the nozzle of the emitter, said cock being able to be introduced into said container by passing through the upper opening of the latter.

Such as is shown in FIG. 5, each treatment station comprises an injection cock 8 mounted in a stationary manner on the plate 110, and which passes through the latter is a substantially sealed manner. This cock extends into the chamber E2, substantially parallel to the nozzle 132 of the emitter, the distal end 80a of the cock being arranged substantially at the same level as the distal end 132a of the nozzle. The cock is used to inject a neutral gas into the container R, such as nitrogen, immediately after the irradiation, in order to create an overpressure in the container R and thus expulse the ozone generated by the irradiation out of the container. Alternatively, the injection of a neutral gas is also carried out during the irradiation.

Alternatively, the cock is used to deliver liquid nitrogen in the container R, for example one drop of liquid nitrogen, during and/or immediately after the irradiation, the liquid nitrogen passing into a gaseous phase then progressively fills the container and progressively removes the ozone from the container.

The gases contained in the chamber, such as air, nitrogen, or ozone, exit via the open ends of the channel. Advantageously, the device comprises a system for overpressuring sterile air, comprising filters that sterilise the air and pumps, in order to provide an overpressure of sterile air in the chamber, in order to remove in particular the ozone from the chamber.

Although the invention has been described in liaison with a particular embodiment, it is obvious that it is in no way restricted to it and that it comprises all of the technical equivalents of the means described as well as combinations thereof if the latter fall within the scope of the invention.

The invention claimed is:

1. Treatment device for sterilizing containers by an electron beam, comprising:
    a carousel comprising a rotary holding plate, supporting a plurality of treatment stations arranged with regular angular spacing, each said treatment station comprising sterilization means which include an electron beam emitter and holding means for holding a container under said emitter, said emitter being able to emit an electron beam passing through an upper opening of a container supported by said holding means in order to sterilize said container,
    a protection system for stopping rays emitted by the emitters, said protection system comprising a protective chamber formed by an open stationary channel mounted under said rotary holding plate; said open stationary channel configured in the form of a ring-shaped segment mounted in a stationary manner under said rotary holding plate, said open stationary channel having a transversal section with at least one of a U and a V shape said open stationary channel having an open upstream end configured as an inlet for the containers, said open stationary channel having an open downstream end configured as an outlet for the containers.

2. Treatment device according to claim 1, wherein said protection system comprises a second system of baffles to shield against the rays that can pass through the upstream and downstream ends of the channel.

3. Treatment device according to claim 2, further comprising a first transfer starwheel, to transfer the containers to be treated to the holding plate upstream of the upstream end, and a second transfer starwheel to remove the treated containers from the holding plate downstream of the downstream end.

4. Treatment device according to claim 3, wherein said second system of baffles comprises a substantially vertical lateral wall extending from an outer wall of the channel, on either side of the upstream and downstream ends, and surrounding the first and second transfer starwheels.

5. Treatment device according to claim 1, wherein the elements that comprise the protection system are made from a lead base.

6. Treatment device according to claim 1, wherein said emitter is provided with a tubular nozzle, able to extend substantially vertically under the holding plate and to deliver via a distal end the electron beam created by the emitter, and each said treatment station comprising means for raising/lowering, acting on said holding means and/or on said emitter in order to introduce said nozzle in the container, via its upper opening, or in order to extract said nozzle from the container.

7. Treatment device according to claim 6, wherein the emitter of each said treatment station is mounted in a stationary manner on the plate, said nozzle extending vertically under the plate, and the means for raising/lowering being able to move said holding means.

8. Treatment device according to claim 6, wherein the emitter of each said treatment station is mounted in a stationary manner on an upper face of the plate, and said protection system further comprising at least one cover covering said emitters.

9. Treatment device according to claim 6, wherein the emitter of each said treatment station is mounted in a stationary manner on a lower face of the plate and is arranged in said protective chamber.

10. Treatment device according to claim 1, further comprising means for injecting a product into the protective chamber in order to remove ozone generated during the irradiation by the electron beam emitters.

11. Treatment device according to claim 10, wherein said means for injecting include an injection cock for each said treatment station, and said cock being able to be introduced into said container by passing through the upper opening of the container.

12. Treatment device of according to claim 1, wherein said stationary channel is substantially without contact with said holding plate, and said protection system comprises a first system of baffles to shield against the rays emitted by the emitters at the plate and the ring segment.

* * * * *